US00PP33492P2

(12) United States Plant Patent
Meilland

(10) Patent No.: US PP33,492 P2
(45) Date of Patent: Sep. 21, 2021

(54) HYBRID TEA ROSE PLANT NAMED 'MEIZOLOI'

(50) Latin Name: *Rosa hybrida*
Varietal Denomination: MEIZOLOI

(71) Applicant: THE CONARD PYLE COMPANY, West Grove, PA (US)

(72) Inventor: Alain Antoine Meilland, Antibes (FR)

(73) Assignee: The Conard Pyle Company, West Grove, PA (US)

( * ) Notice: Subject to any disclaimer, the term of this patent is extended or adjusted under 35 U.S.C. 154(b) by 0 days.

(21) Appl. No.: 17/128,569

(22) Filed: Dec. 21, 2020

(51) Int. Cl.
*A01H 5/02* (2018.01)
*A01H 6/74* (2018.01)

(52) U.S. Cl.
USPC ..... Plt./130
CPC ..... *A01H 6/749* (2018.05)

(58) Field of Classification Search
USPC ..... Plt./130
CPC ..... A01H 6/749; A01H 5/02
See application file for complete search history.

(56) References Cited

U.S. PATENT DOCUMENTS

PP14,731 P3 4/2004 Twomey
PP18,102 P2 10/2007 Lim

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of hybrid tea rose plant, referred to by its cultivar name, 'MEIZOLOI', is disclosed. The new variety forms on a nearly continuous basis attractive, cup shaped, yellow with pink edged colored flowers. Attractive, dark green and glossy foliage is formed, which contrasts beautifully with the blossoms. An erected growth habit is displayed. The new variety is well suited for providing attractive ornamentation in the landscape.

1 Drawing Sheet

Botanical/commercial classification:
Latin name—*Rosa hybrida.*
Varietal denomination—'MEIZOLOI'.

SUMMARY OF THE INVENTION

The new variety of *Rosa hybrida* plant was created by artificial pollination in Le Cannet des Maures, Var, France wherein two parents were crossed which previously had been studied in the hope that they would contribute the desired characteristics. The female parent (i.e., the seed parent) was the 'BAICENT' variety (U.S. Pat. No. 18,102). The male parent (i.e., the pollen parent) was an unnamed seedling (non-patented).

The parentage of the new variety can be summarized as follows:

'BAICENT' x Unnamed Seedling

The seeds resulting from the above pollination were sown and small plants were obtained which were physically and biologically different from each other. Selective study resulted in the identification of a single plant of the new variety.

It was found that the new variety of rose plant of the present invention possesses the following combination of characteristics:

(a) forms yellow with pink edged colored flowers, and
(b) exhibits a dark green, glossy foliage.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'BAICENT' variety (i.e., the seed parent) displays a light yellow colored flowers, whereas the new variety displays yellow with pink edged colored flowers. The unnamed seedling male parent (i.e., the pollen parent) displays dark pink colored flowers, whereas the new variety displays yellow with pink edged colored flowers. Moreover, the new variety can be readily distinguished from other similar non-parental varieties. For example, the 'BAIPEACE' variety (U.S. Plant Pat. No. 14,731) displays less flowering (blooming) and a higher plant growth habit compared to the new variety.

The new variety has been found to undergo asexual propagation in Le Cannet des Maures, Var, France by a number of routes, including softwood cuttings and grafting t-bud. Asexual propagation by the above-mentioned techniques in Le Cannet des Maures, Var, France has shown that the characteristics of the new variety are stable and are strictly transmissible by such asexual propagation from one generation to another. Accordingly, the new variety undergoes asexual propagation in a true-to-type manner.

The new variety has been named 'MEIZOLOI'.

The first offer for sale of the new variety was Jan. 24, 2020 in the United States of America by the inventor or another who obtained the new variety directly or indirectly from the inventor.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately five years of age and were observed during June while budded on their own roots and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—reverse.

Element 7—illustrates a specimen of an open flower—plan view—observe.

Element 8—illustrates a specimen of a fully open flower—plan view—reverse.

Element 9—illustrates a specimen of a fully open flower—plan view—observe.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—under surface.

Element 14—illustrates a specimen of a leaf with 7 leaflets—plan view—under surface.

Element 15—illustrates a specimen of a leaf with 5 leaflets—plan view—under surface.

Element 16—illustrates a specimen of a leaf with 5 leaflets—plan view—upper surface.

Element 17—illustrates a specimen of a leaf with 7 leaflets—plan view—upper surface.

Element 18—illustrates a specimen of a leaf with 3 leaflets—plan view—upper surface.

DETAILED BOTANICAL DESCRIPTION

The chart used in the identification of the colors is that of The Royal Horticultural Society (R.H.S. Colour Chart, 2001 edition), London, England. The terminology which precedes reference to the chart has been added to indicate the corresponding color in more common terms. The description is based on the observation of five-years-old specimens of the new variety during June while budded on their own roots and growing outdoors at Le Cannet des Maures, Var, France.

Commercial classification: Hybrid Tea Rose Plant.

Plant:

*Habit*.—Erected.

*Height*.—Approximately 60 cm on average.

*Width*.—Approximately 50 cm on average.

Branches:

*Color*.—Young stems: commonly near Yellow-Green Group 144A. Adult wood: commonly near Yellow-Green Group 146A.

*Length of main stem*.—Typically 20 to 50 cm on average.

*Young shoots*.—Anthocyanin coloration: weak intensity and commonly near Greyed-Orange Group 176A.

*Thorns*.—Configuration on adult stems: concave, slightly curved downwards and elongated on the upper surface and oval, narrow and elongated on the under surface. Long prickles — quantity: commonly approximately 6 thorns per 10 cm long young stem and commonly 7 thorns per 10 cm long adult stem. Long prickles — base shape: concave. Long prickles — size: typically 0.8 to 0.9 cm in length on average on young stems and adult stems. Long prickles — color: commonly near Yellow-Green Group 153A suffused with near Greyed-Orange Group 171A on young stems and commonly near Greyed-Orange Group 165B on adult stems. Small prickles — quantity: absent.

Foliage:

*General appearance*.—Dense with glossy aspect.

*Number of leaflets*.—3, 5, and 7; most often 5.

*Terminal leaflet*.—Length: typically 3.5 to 6.0 cm on average. Width: typically 2.0 to 3.7 cm on average.

*New foliage*.—Upper surface color: commonly near Green Group 137C more or less suffused with near Greyed-Orange Group 176A. Under surface color: commonly near Green Group 137D more or less suffused with near Greyed-orange Group 176A.

*Adult foliage*.—Upper surface color: commonly a mix between near Green Group 137A and near Green Group 139A. Under surface color: commonly near Green Group 137d.

Leaflets:

*Shape*.—Tip: cuspidate. Base: obtuse.

*Glossiness of upper surface*.—Medium.

*Texture*.—Leathery.

*General appearance*.—Oval.

*Edge*.—Slightly obtuse.

*Serration*.—Small and single.

*Undulation on the margin*.—Weak.

*Petiole rachis*.—Color of upper surface: commonly near Green-White Group 157D. Color of under surface: commonly near Green Group 139C.

*Petioles*.—Upper surface: few glandular. Under surface: few prickles. Color of upper surface: commonly near Green Group 139C. Color of under surface: commonly near Yellow-Green Group 144A. Petiole length of terminal leaflet: typically 2.2 to 4.0 cm on average.

*Stipules*.—General appearance: adnate, pectinate and narrow. Length: approximately 1.2 cm on average. Width: typically 0.1 to 0.2 cm on average. Color of upper surface: commonly near Green Group 137B. Color of under surface: commonly near Green Group 137D.

Inflorescence:

*Number of flowers per stem*.—Typically 1 flower per stem.

*Lastingness of the bloom*.—On the plant: approximately one week on average.

*Bud*.—Shape: conical. Size: medium. Length: typically 2.5 to 3.0 cm on average. Width: typically 2.5 to 3.0 cm on average. Color as calyx breaks: upper surface: commonly near Yellow Group 13B edged with near Red Group 47B. under surface: commonly between near Yellow Group 13B and Yellow Group 13C, edged with Red Group 47A.

*Sepals*.—Length: approximately 2.5 cm on average. Width: approximately 1.0 cm on average. Shape: at the top: elongated and narrow, at the base: upright and broad. Extensions: some, elongated, length is typically 0.5 to 0.7 cm and width is approximately 0.1 cm on average. Upper surface: texture: smooth. color: commonly near Green Group 143C. Under surface: texture: tomentous. color: commonly near Yellow-Green Group 145D suffused with near Red Group 47A.

*Receptacle*.—Color: commonly near Green Group 143C. Length: approximately 0.8 cm on average. Width: approximately 1.0 cm on average. Surface: smooth. Shape: funnel shaped.

*Peduncle*.—Length: approximately 3.5 cm on average. Width: approximately 0.3 cm on average. Surface: very slightly glandular. Color: commonly near Green Group 143C.

*Flower*.—Average diameter when fully open: typically 10 to 12 cm on average. Shape: cup shaped. Type: double. Number of petals under normal conditions: approximately 40 petals on average. Shape of the petal: base: obtuse. top: rounded and slightly cordate. Texture of the petal: slightly crumpled. Petal length: approximately 3.0 to 3.5 cm on average. Petal width: approximately 3.0 to 4.0 cm on average. Petal arrangement: imbricated without petaloids. Petal drop: petals drop off cleanly before drying. Fragrance: weak. Color when opening: spot at the base: commonly near Yellow Group 5A. upper surface of the flower: commonly near Yellow Group 5C suffused and edged with near Red Group 48B. under surface of the flower: commonly near Yellow Group 2D edged with near Red Group 47A. Color of the open flower: spot at the base: commonly near Yellow Group 5A. upper surface of the flower: commonly near Yellow Group 5C edged with near Red-Purple Group 62B and edged with near Red-Purple Group 57C on the external petals. under surface of the flower: commonly near Yellow Group 2D slightly edged with near Red-Purple Group 62B. Anthers: number is approximately 175 on average, length is approximately 0.2 cm on average, coloration is commonly near Yellow-Orange Group 17A, and arrangement is regular around styles. Filaments: length is approximately 0.2 cm on average and coloration is commonly near Yellow Group 7A. Styles: length is approximately 0.1 cm on average, coloration is commonly near Green-White Group 157A, and number is approximately 250 on average. Stigmas: size is approximately 0.1 cm on average and coloration is commonly near Yellow-Orange Group 20A. Pollen: color is commonly near Greyed-Orange Group 163A. Hips: not available at this stage.

Development:

*Vegetation*.—Strong.

*Blooming*.—Early in the season, very abundant and nearly continuous, typical from May to October in France.

*USDA hardiness zone*.—Zone 5.

*Tolerance to disease*.—Very good, and particularly against black spot (*Diplocarpon rosae*).

The new 'MEIZOLOI' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEIZOLOI' characterized by the following combination of characteristics:

(a) forms yellow with pink edged colored flowers, and (b) exhibits a dark green, glossy foliage;

substantially as herein shown and described.

* * * * *

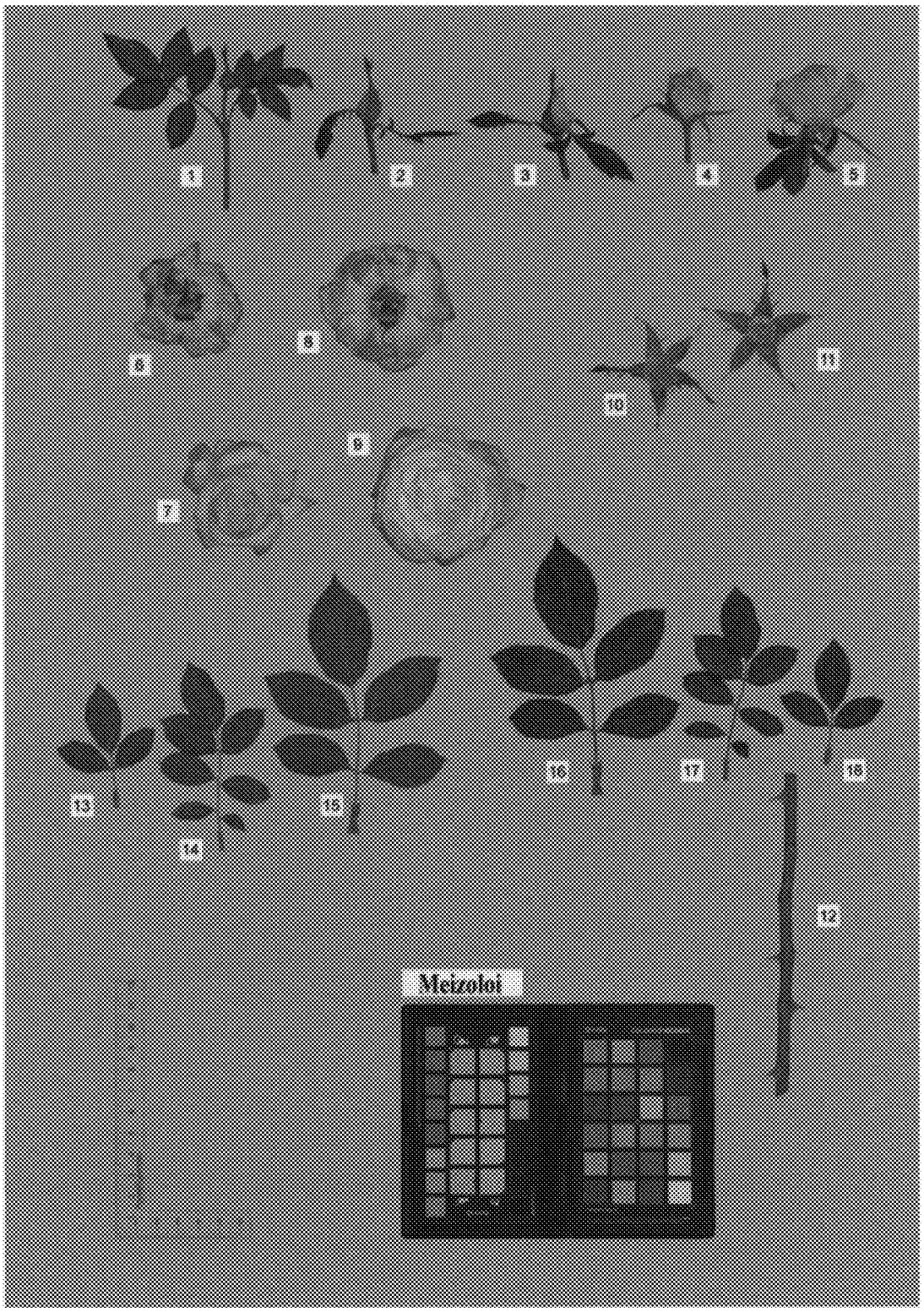
1
2
3
4
5
6
7
8
9
10
11
12
13
14
15
16
17
18
Meizolai